United States Patent
Gouge et al.

[11] Patent Number: 6,067,371
[45] Date of Patent: May 23, 2000

[54] METHOD AND SYSTEM FOR NON-INVASIVE TEMPERATURE MAPPING OF TISSUE

[75] Inventors: James Gouge, Summerville, Ga.; Everette C. Burdette, Champaign, Ill.; Richard diMonda, Marietta, Ga.

[73] Assignee: Dornier Medical Systems, Inc., Kennesaw, Ga.

[21] Appl. No.: 09/022,797

[22] Filed: Feb. 13, 1998

Related U.S. Application Data

[63] Continuation-in-part of application No. 08/563,570, Nov. 28, 1995, abandoned.

[51] Int. Cl.$^7$ ........................................... G06K 9/00
[52] U.S. Cl. .......................... 382/128; 382/218; 606/412; 606/549
[58] Field of Search ........................... 382/128, 157, 382/218; 600/412, 549

[56] References Cited

U.S. PATENT DOCUMENTS

| | | | |
|---|---|---|---|
| 4,620,546 | 11/1986 | Aida et al. | 128/660 |
| 5,267,328 | 11/1993 | Gouge | 382/16 |
| 5,370,121 | 12/1994 | Reichenberger et al. | 128/660.02 |

FOREIGN PATENT DOCUMENTS

| | | | |
|---|---|---|---|
| 0627206 | 3/1994 | European Pat. Off. | A61F 7/00 |

*Primary Examiner*—Matthew Bella
*Attorney, Agent, or Firm*—Jones & Askew, LLP

[57] ABSTRACT

A method and system for mapping temperature from image data. The method includes the steps of: receiving an image of tissue comprised of multiple pixels, segregating the image into groups of pixels (104), each group of pixels having a set of descriptors (106), establishing a baseline set of descriptors corresponding to initial conditions of the imaged tissue (108), measuring a differential in the set of descriptors for a group of pixels (114), the differential corresponding to a change in pixel values for the group of pixels, correlating said measured differential to a temperature change for the tissue corresponding to the group of pixels (118–124), and overlaying an indication of temperature over the tissue image in response to said correlated temperature change indicating a change in temperature range for the tissue (130–132). The system includes a digital processor implementing a neural network for evaluating a set of descriptors against baseline values learned by the neural network form the initial conditions of the tissue.

14 Claims, 4 Drawing Sheets

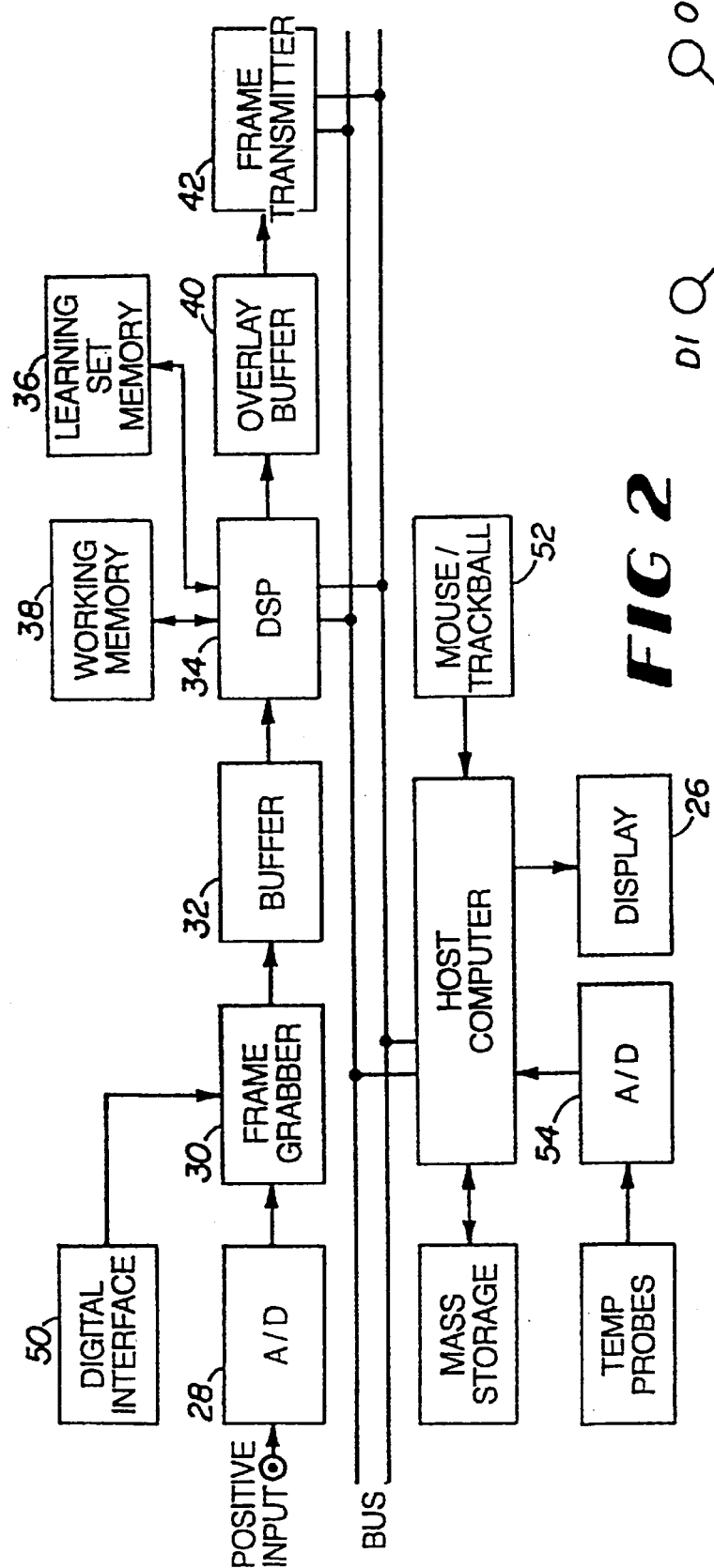
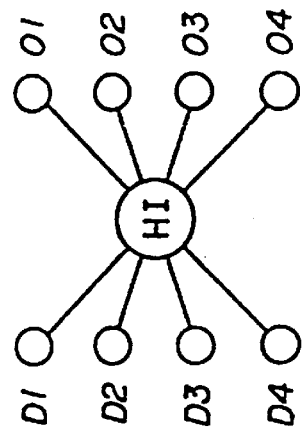
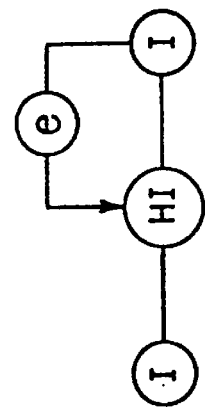
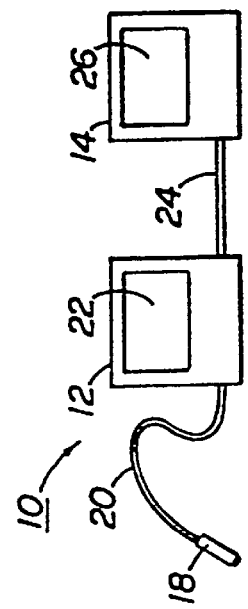

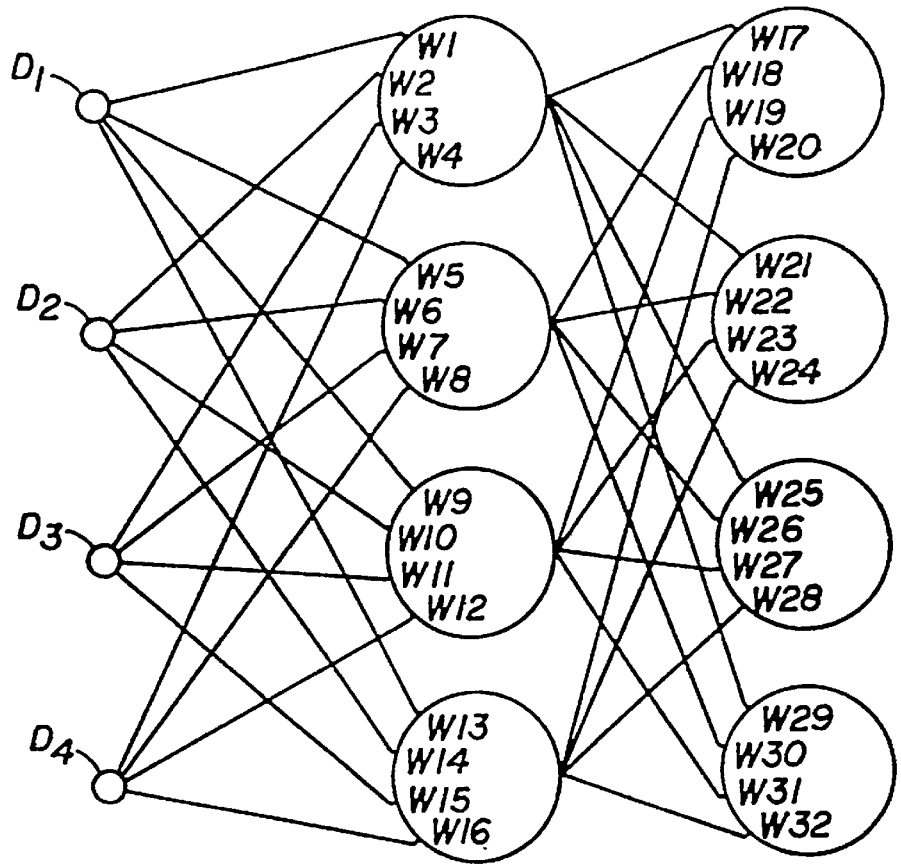
*FIG 3C*
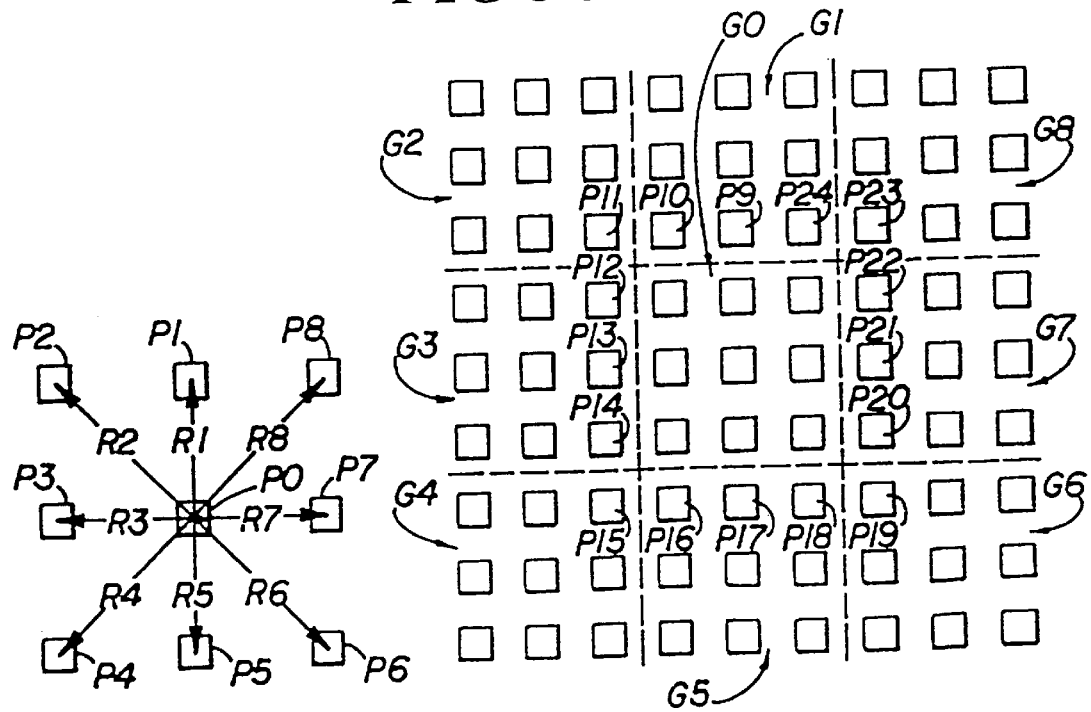
*FIG 4A*   *FIG 4B*

//<sub></sub>

METHOD AND SYSTEM FOR NON-INVASIVE TEMPERATURE MAPPING OF TISSUE

This application is a continuation-in-part of application Ser. No. 08/563,570 filed on Nov. 28, 1995, now abandoned.

FIELD OF THE INVENTION

This invention relates to temperature monitoring equipment and methods, and more particularly, to methods and systems for monitoring the temperature of tissue.

BACKGROUND OF THE INVENTION

Methods and systems for treating tissues using heat therapy or hyperthermia are well known. For example, the treatment of cancerous tissue with heat is know to be beneficial. Specifically, heating such abnormal tissue above a threshold temperature of approximately 42° Celsius introduces irreversible cellular damage to the tissue. In this manner, benign and malignant tumors may be necrosed. At temperatures above 45° Celsius, irreversible damage occurs not only to abnormal tissue but to healthy tissue as well. The temperature range of approximately 42–45° Celsius is known as the therapeutic hyperthermic range for human tissue. Heat therapy in the range of 45–60° Celsius is generally known as thermal therapy or thermotherapy. At temperatures above 65° C., tissue is ablated.

While the generally recognized temperature range for necrosing abnormal tissue is well known, a number of other factors may affect the influence of heat on specific tissue. For example, if the tissue has an abnormally low cellular pH, poor oxygenation, or nutritional deprivation, the tissue is more likely to be vulnerable to irreversible damage at temperatures lower than normally expected. This is one of the reasons that abnormal or neoplastic tissues are thought to be more susceptible to temperature increases than normal tissue.

To supply heat to abnormal tissue to hyperthermally treat the tissue, both external noninvasive and Minimally Invasive Surgery ("MIS") techniques and technology have been developed. Non-invasive induction techniques use radiofrequency (RF) and microwave applicators as well as ultrasound transducers. The MIS techniques and technology largely involve inserting therapy probes into the body which emit energy directed to a target area of tissue to destroy the diseased tissue. The energy types emitted by the probes are typically laser, microwave, RF, electrocautery, or ultrasound in nature. These probes are placed proximate the abnormal target tissue for administration of the energy either through interstitial, intracavitary or laproscopic methods. Interstitial placement of a probe means that the probe, usually introduced by a needle or catheter, is placed directly into the tissue. An intracavitary method requires that the probe be placed in a natural body opening proximate the target tissue and laproscopic surgery requires a small incision which permits the placement of the probe proximate the target tissue. For example, a thermal therapy probe may be used to treat a prostate cancer by inserting the probe through the perineum or urethra into the diseased area (interstitial), into either the urethra or rectum and directed toward the target area (intercavitary), or through a laproscopic incision to allow placement of the probe near the tissue. Such exemplary methods may be used to place probes for the emission of energy into abnormal tissues to treat, for example, non-resectable liver cancer, prostate cancer, pancreatic cancer, breast cancer and various gynecological diseases.

While these MIS techniques permit energy emitting probes to be placed proximate the tissue to be treated so that the tissue contacted by the emitted energy is heated, there has been little provision for the monitoring of temperature either at the target area or in the neighboring areas. As a result, a treating physician may have difficulty in determining whether an adequate thermal dosage has been applied to the target area to sufficiently necrose or ablate the abnormal tissue without affecting the surrounding normal tissue. If the treating physician fails to supply a sufficient dosage of a thermal treatment to destroy all of the abnormal tissue, then the surviving abnormal tissue may regenerate and the cancer or other abnormal cellular condition may continue. On the other hand, if the physician applies more than an effective dosage of the thermal treatment, then the amount of normal tissue affected by the treatment may increase morbidity or cause side effects which adversely impact the patient's health.

In response to this need to effectively determine the dosage of the thermal treatment, various attempts have been made to measure the thermal dosage or its effects. One such attempt has been to time the emission of the energy which generates the thermal effect in the tissue for a predetermined period of time. This timing constraint, however, relies upon assumptions about both the abnormal tissue and the condition of the normal tissue surrounding the target area. To compensate for different tissue conditions caused by age, the patient's general health, oxygenation of the surrounding tissue, blood perfusion in the surrounding tissue, and other known parameters which affect the energy absorption rates and therapeutic dosage achieved in the target tissue, empirical studies are necessary. These studies are used to provide general parameters which, at best, can only provide estimated times for a thermal dosage. Thus, use of a predetermined time to control the dosage of the thermal treatment to a target area in the absence of adequate monitoring of the treatment may result in ineffective treatment of the abnormal tissue or may result in the unnecessary destruction of healthy tissue.

In an effort to supply some feedback of temperature data from the target area and surrounding area, other methods for monitoring tissue temperature have been developed. One such method requires the implantation of temperature probes in the tissue to provide information regarding temperature in the affected tissue area. Placement of these temperature probes is a delicate operation and knowledge of the exact location of the probes and sensors is essential to accurately discern temperatures within the target tissue and outside the target region as well as to extrapolate temperatures for the area surrounding the probes and sensors. Additionally, the placement of these probes requires invasive techniques and further requires the removal of these probes after treatment. Of course, these invasive techniques and the placement of the temperature probes within the tissue add to the invasive nature of the overall procedure and may cause trauma from which the patient must heal. Additionally, heat is conducted from the treated area outwardly to the surrounding tissue at different rates primarily due to differing perfusion levels and energy absorption rates by different tissue types. The effective monitoring of the heating within and surrounding the treated area may require a number of probes which a treating physician may not consider practical or clinically acceptable. Another factor affecting the effectiveness of temperature probes is the different thermal conductivity of healthy tissue versus that of abnormal tissue. Normally, the temperature probes are placed in the healthy tissue surrounding an affected area. As a result, the rate of transfer of heat from the target area to the healthy tissue area may cause the thermal probe to not register a higher temperature until tissue between the probe and the abnormal tissue area has already been destroyed. Thus, the location of temperature probes within the normal tissue is important and may affect the effectiveness of the thermal treatment.

Another attempt to provide temperature monitoring during thermal therapy techniques includes the use of magnetic resonance imaging to display temperature changes in tissue. Magnetic resonance imaging techniques are typically cost prohibitive as they require the use of special non-magnetic instruments and facilities to perform such procedures. Accordingly, the use of such technology appears to be limited to very special environments, instrumentation, and to procedures which require imaging of relatively large areas.

Finally, some attempts have been made to utilize ultrasound imaging for thermal therapy monitoring. Ultrasound data is typically expressed in grayscale pixel data which is used to image tissue structure in various shades of gray. The changes in tissue structure as abnormal tissue is necrosed or ablated are not significant enough to perceptually change the displayed image. In a similar manner, the structural change within normal tissue as its temperature approaches the destructive threshold where universal cellular damage occurs, may not be directly observable in a typical grayscale ultrasound image.

What is needed is a way to monitor the temperature of tissue in a hyperthermic or thermally treated target area and vicinity.

What is needed is a way of monitoring thermal conditions in tissue without requiring placement of numerous temperature probes or the careful placement of such probes in the target and surrounding tissues.

What is needed is a way of monitoring and displaying temperature data for tissue in the area of thermally treated tissue which does not require cost-prohibitive magnetic resonance instrumentation and environment.

What is needed is a way of monitoring the temperature of tissue with ultrasound energy which provides temperature data or tissue damage information even though the structural characteristics of the tissue are not visually perceptible or significantly altered by the temperature change occurring in the tissue.

SUMMARY OF THE INVENTION

The limitations of the previously known systems and methods for monitoring tissue temperature have been overcome by a system and method performed in accordance with the principles of the present invention. The method of the present invention includes the steps of: receiving an image of tissue comprised of multiple pixels, segregating the image into groups of pixels, each group of pixels having a set of descriptors, establishing a baseline set of descriptors corresponding to initial conditions of the imaged tissue, measuring a differential in the set of descriptors for a group of pixels, the differential corresponding to a change in pixel values for the group of pixels, correlating said measured differential to a temperature change for the tissue corresponding to the group of pixels, and overlaying an indication of temperature over the tissue image in response to said correlated temperature change indicating a change in temperature range for the tissue.

This method may be implemented by a system made in accordance with the principles of the present invention. Such a system includes an ultrasound display device and temperature mapping workstation for reading image data generated by the ultrasound display device and for interpreting changes in the image data. Preferably, at least one temperature probe is inserted in the tissue within the imaged area and most preferably, the probe is placed in the target area. The temperature mapping workstation reads the ultrasound display pixels for the imaged tissue area and uses one of several edge detection techniques such as simple threshold, gradient detection, Canny detection, radial analysis or the like to acquire baseline values and probability histograms to detect image changes which may be correlated to temperature measurements. The entire image or a preselected portion of the image may be analyzed. The intensity level of the ultrasound image is preferably adjusted so that the lightest pixels displayed may change to a grayscale value which corresponds to the ablative temperature threshold prior to exceeding the lightest grayscale value. After the grayscale intensity is adjusted, a set of baseline descriptors is defined for each group of pixels. Each group of pixels also has a number of neural elements corresponding to the number of descriptors in the set of descriptors. The output of the neural elements for a group of pixels is coupled to output neural elements. Each output neural element corresponds to one of the possible temperature ranges for the tissue. The weighing of the outputs from the neural elements for a group of pixels at each output element results in one of the output elements being activated to indicate the temperature for the group of pixels. Preferably, pixel values read before the initiation of thermal treatment are used to develop a learning set of data to establish the weights for the neural elements. Each output neural element compares its activation state with the normal temperature to provide an adjustment signal to the weights used by the neural elements for a group of pixels, if an output element detects an error.

Once the thermal treatment begins, the tissue receives energy from the treatment probe causing the tissue to heat. The temperature change in the tissue in turn affects the backscattered ultrasound imaging energy. Consequently, the pixel data being generated by the ultrasound display device to update the image of the tissue also changes. Tissue temperature is measured by the probe and the temperature change is plotted against time. This temperature change is compared to the corresponding change in the weighted average grayscale value for the set of descriptors for the group of pixels corresponding to the location where the probe has been placed. The correlation between grayscale change and temperature change is provided to the neural elements for the other neural elements in the system. Multiplying the differential between the baseline grayscale weighted average and the current grayscale weighted average by the correlation factor, each neural element provides a signal corresponding to a temperature for its corresponding group of pixels. This temperature is compared to the thresholds for each of the temperature ranges to determine the range in which the group of pixels resides. The mapping system generates an overlay for the displayed image which indicates a predetermined temperature zone for the tissue represented by each group of pixel values. When the temperature mapping system determines that a measured differential correlates to a temperature in a different temperature zone, the overlay is updated to indicate the new temperature zone for the tissue represented by the group of pixels.

Preferably, the mapping system uses edge detection techniques to establish baseline measure differentials. The detected edges may be counted, gradients between edges measured or differences between edges accumulated to establish baseline values. One or more of such values associated with edges may be used to establish baseline values. Any of a number of edge detection techniques of varying degrees of sophistication may be utilized such as simple threshold detection, gradient detection, and Canny edge detection. The detected edges may be used in turn to identify linear boundaries and recognizable shapes. Directional paths through a group of pixels may be used to select pixels for edge detection. The pixels associated with different paths may yield differing degrees of information. Each descriptor path yields a different probability distribution, and there is less information overlap if the probabilities are orthogonal.

Another method which may be implemented in the system of the present invention segregates a group of pixels in an initial image of tissue into a target area, extracts pattern data from the target area to establish a baseline for each pattern in the extracted pattern data, extracts pattern data from a corresponding target area in a subsequent image of the tissue, determines a best correspondence between the extracted pattern data in the subsequent image and the extracted pattern data in the initial image, measures a differential between the extracted pattern data from the subsequent image and the established baseline for the best corresponding pattern data in the initial image, and correlates a temperature change to the measured differential to determine the temperature change for the extracted pattern data in the subsequent image. The temperature change determined for the extracted pattern data in the subsequent image may be used to compute an absolute temperature for the tissue corresponding to the extracted pattern data. The range in which the absolute temperature resides may then be identified on a system display by overlaying the subsequent image with an indication of the temperature range.

The geometric shapes extracted from the initial and subsequent images are determined by extracting radial data about target pixels and line data for the target pixels. The radial data includes radial shape data, radial spatial distribution data, radial contour data, radial asymmetry data, and radial gradient data, all of which are extracted from target pixels corresponding to an extracted geometric shape. This radial data and the line data extracted from the images are obtained using the method disclosed in U.S. Pat. No. 5,267,328 to Gouge (the "'328 Patent). The Gouge method encodes geometric shape data from images in an efficient manner which permits the system of the present invention to be implemented on an IBM personal computer. As disclosed in the '328 Patent, the encoded data may be represented by bit streams organized in a knowledge tree. This knowledge tree of data for an extracted geometric shape from an initial image is used to form the baseline for the extracted geometric shape. Correlation factors obtained from empirical measurements of temperature obtained with temperature probes for successive images analyzed by the system are used to correlate a differential measurement to a temperature change for a geometric shape in a subsequent image.

During the thermal treatment of the tissue, the tissue receiving the thermal radiation begins to change and the corresponding pixel values in the displayed image change. Heretofore, that change has been relatively imperceptible to a viewing physician and has not provided an adequate indication of the dosage of the thermal treatment which the target area is receiving. The changes from the baseline values for a set of descriptors for a group of pixels are measured and correlated to temperature changes of the tissue within the displayed image. One method for correlation of thermally-induced changes utilizes Chamfer Matching techniques, which provides volume set correlation between images. The temperature changes are compared to threshold temperature for different temperature ranges to determine in which range the group of pixels reside. A color overlay which indicate the temperature range within which each group of pixels reside is then generated and transmitted for display with the image. Another method of generating this overlay is to correlate a color to each temperature range. For thermal treatment of tissue the temperature ranges of interest are the normal, hyperthermic, thermal therapeutic, and ablative. Preferably, the values associated with these ranges are grayscale, brown, green, and red, although other colors may be used.

Preferably, the mapping system correlates changes in the baseline value for the group of pixels corresponding to tissue where a temperature is implanted with temperatures measured by the probe. This grayscale-to-temperature correlation factor is preferably expressed as a ratio of grayscale units to degrees Celsius. This correlation factor may then be used to modify the grayscale-to-temperature correlation factors for other groups of pixels. In this manner, the mapping system detects temperature changes in each tissue area associated with a group of pixels without requiring that a temperature probe be implanted in each tissue area. This permits the expert system to detect thermal changes in tissue surrounding the targeted area which result from predominantly thermally-induced tissue changes, and include blood perfusion, increased oxygenation, and other factors occurring as a result of the thermal treatment of the targeted area. As a result, the mapping system need not utilize assumptions about the absorption rate of the tissue to generate the temperature overlay but rather learns how to correlate the pixel changes to temperature measurements during treatment.

The advantages of the present invention include the ability to monitor temperature treated tissue without requiring placement of numerous temperature probes. If temperature probes are desired for verification of the temperature monitoring, the number of probes needed to verify the mapping system's operation is significantly reduced over systems which rely only upon temperature probes to indicate tissue temperature. The system and method of the present invention permit a treating physician to detect temperature changes in tissue which lie within the display of the ultrasound device which may be affected by the application of the thermal treatment in the targeted area. Thus, a treating physician may detect tissue changes in areas other than the target area which may affect the physician's decision to continue to treat the targeted area. By observing color changes in the display, the treating physician may identify tissue which has been ablated, tissue at or approaching thermal necrosing, and tissue which remains within the normal temperature zone. In response to this information, a viewing physician has more control over the placement of the energy emitting probe to ensure the destruction of abnormal tissue without raising the temperature of healthy tissue to a point of thermal damage.

Another advantage of the present invention is that magnetic resonance imaging is not required for temperature mapping. As a result, this cost-prohibitive MRI method of temperature profiling is avoided and the cost of healthcare is significantly reduced over methods utilizing such temperature monitoring techniques.

These and other advantages and benefits of the present invention may be ascertained by a review of the accompanying drawings and the detailed description.

BRIEF DESCRIPTION OF THE DRAWINGS

FIG. 1 is a block diagram of a system which monitors the temperature of tissue displayed on an ultrasound device;

FIG. 2 is a block diagram of a temperature mapping workstation used in the preferred embodiment of the present invention;

FIG. 3A is a schematic diagram of a neural element;

FIG. 3B is a schematic diagram of an exemplary neural element using four descriptors to determine a temperature for a pixel or group of pixels;

FIG. 3C is a schematic diagram of a neural network of groups of pixels shown in FIG. 3B;

FIG. 4A is a schematic diagram of the pixels used to define a set of descriptors for a pixel;

FIG. 4B is a schematic diagram of the pixels used to define a set of descriptors for a group of pixels;

DETAILED DESCRIPTION OF THE INVENTION

Figure 5:
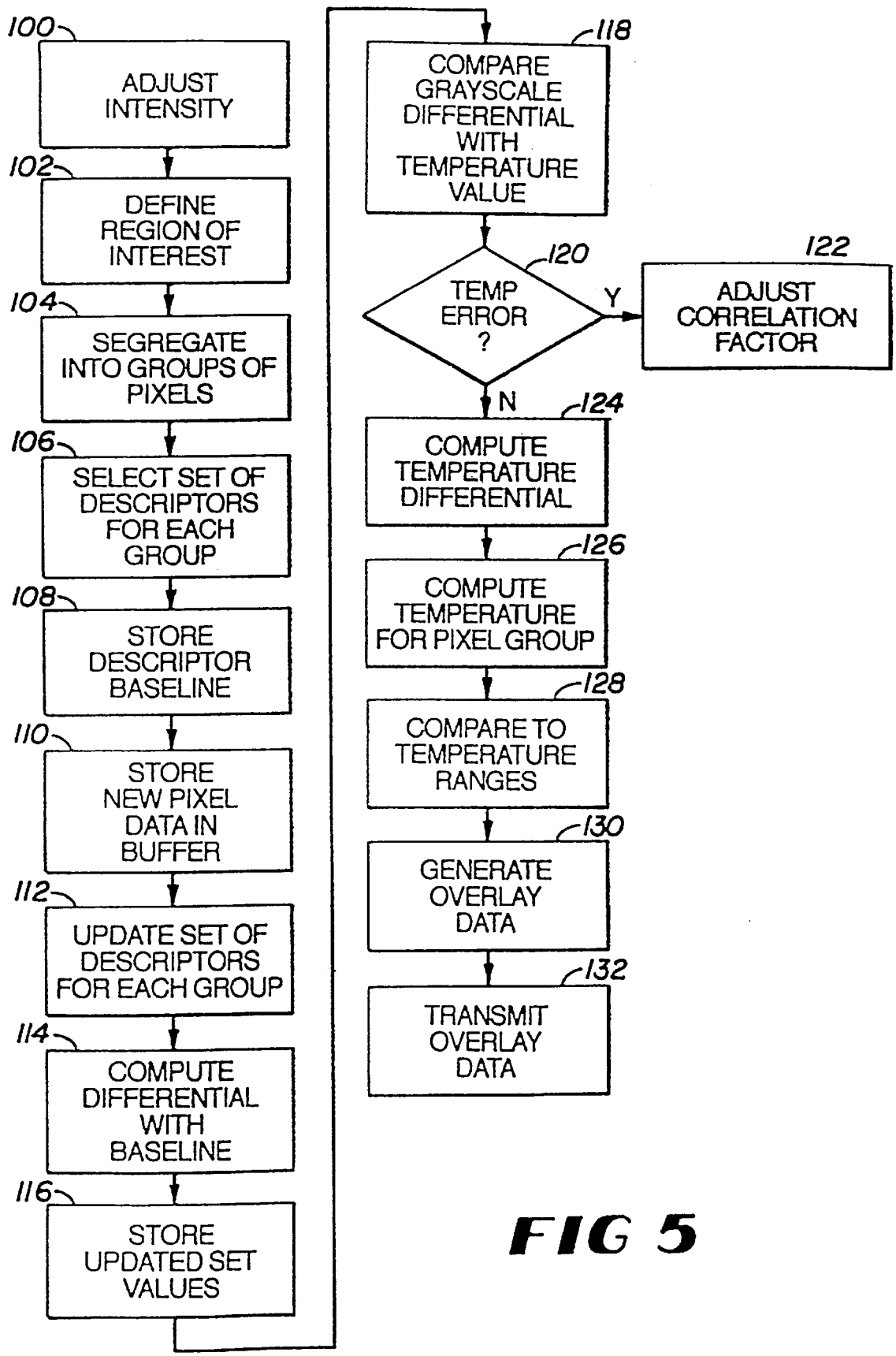
FIG. 5 is a flowchart of a method for monitoring temperature of tissue displayed on an ultrasound device.

A system which may be used to implement the principles of the present invention is shown in FIG. 1. The system 10 includes an ultrasound imaging device 12 to which a temperature mapping workstation or system 14 is coupled. The ultrasound imaging system 12 includes a computer unit 16 and a transmitter/transducer unit 18. The transmitter/transducer unit is coupled to the computer unit through an electrical cable 20. The transmitter/transducer unit 18 emits ultrasound energy and receives the energy backscattered by the tissue. This information is provided to computer unit 16 which processes the backscattered data to generate images displayed on display 22. Such ultrasound imaging systems are well known within the art. The temperature mapping workstation 14 is shown coupled to computer unit 16 for communication of image data through an electrical cable 24. Alternatively, the image processing performed by temperature mapping workstation 14 may be implemented on a digital signal processing card coupled through a system bus or the like to system 12.

System 10 of the present invention may be used in conjunction with a thermal treatment device such as a microwave, laser, RF, electrocautery, or ultrasound probe, but the use of the system 10 is not limited to such applications. For example, the system 10 may be used to monitor the temperature of tissue which is responding to a chemical either injected into the tissue or taken intravenously.

The display of image data on the screen of an ultrasound imaging device is well known. Basically, ultrasound energy is emitted from the transmitter portion of transmitter/transducer unit 18 towards the tissue to be displayed. This energy is backscattered differently by different types of tissue. This backscattered ultrasound energy is comprised of spectral reflection and interference reflection portions. The backscattered energy is received by the transducers of transmitter/transducer 18 and converted to grayscale intensity data. The grayscale intensity data is stored in a video RAM or the like within system 12. Such RAMs are well known and are typically organized in a row and column manner which corresponds to the pixels for display screen 22. The grayscale intensity data is retrieved from video RAM 22 or the like and used to generate the driving signal for the display screen 22. The retrieval of the grayscale data and generation of the driving signal is performed at a rate so the screen does not appear to "flicker" to the human eye.

Video RAMs are normally constructed so that a processor may update pixel values within the RAM in an interleaved fashion with the reading of data from the video RAM for driving the display. Most commercially available ultrasound systems provide a video data port so the signal used to drive display 22 may be recorded. This port is typically a RS-170 port and the data provided through such ports are well known.

Preferably, mapping workstation 14 receives the video data signal from the video data port and digitizes the signal to generate pixel data. Since most ultrasound systems have a RS-170 port, such an implementation makes workstation 12 compatible with most ultrasound systems. Alternatively, workstation 14 may couple to system 12 through a parallel or serial data port to communicate pixel or grayscale data with system 12. This structure has the advantage of providing grayscale data from system 12 prior to the data undergoing signal processing in system 12. The system 12 may perform signal processing which reduces sensitivity to the information available in the interference reflection component of the backscattered energy. This reduction in sensitivity may affect the accuracy of the temperature detection by workstation 14. By obtaining pixel data prior to the ultrasound imaging system processing it, the information in the reflection component may contribute to more accurate temperature mapping. Additionally, pixel data generated by system 12 may contain manufacturer specific information that may complicate its processing for the temperature mapping. The transfer of either analog or digital image data or their equivalents for temperature mapping is within the principles of the present invention.

Grayscale data is a data word which defines an intensity level for a pixel of a display. The lowest value of the grayscale range corresponds to a low intensity or black shade pixel while the high value of the range corresponds to the brightest intensity or white shade pixel. The intervening values are a shade of gray, hence the term grayscale data. Grayscale data may be displayed on a screen capable of displaying color data. Display 22 of ultrasound unit 12 and display 26 of workstation 14 are displays capable of displaying both grayscale and color images.

Preferably, temperature mapping workstation 14 is a personal computer or the like with an Intel Pentium processor, 8 MB or more of RAM and a 540 or larger MB hard drive. Coupled to system 14 through its system bus is a digital processing card which processes the image data from system 12 to perform the temperature mapping. One such digital signal processor card is manufactured by Coreco of Saint Laurent, Quebec, Canada which is designated as an Oculus F/64 digital signal processing card. The image data to be processed may be displayed on display 26 of system 14. Additionally, system 14 may include standard input/output (I/O) devices such as a mouse or trackball for moving a cursor about the image displayed or display 26 and for identifying coordinates on the image.

FIG. 2 is a block diagram of a digital signal processing card 28 used to implement the temperature mapping of the present invention. The card includes a frame grabber 30, a data buffer 32, a data signal processor 34, a learning set memory 36, a working memory 38, a overlay buffer 40 and a frame transmitter 42. Frame grabber 30 retrieves video data from a video data port one frame at a time and converts the analog video data to pixel data which is stored in data buffer 32 for processing. Alternatively, frame grabber 30 may receive data from a digital interface 50 which communicates with system 12 through a digital data port to obtain grayscale data generated by system 12. The grayscale data is used by system 12 to produce the video signal which drives display 22 and may or may not undergo digital signal processing prior to its transfer to workstation 14. Typically, frame data is provided to display 22 at a rate of approximately 9 to 20 frames a second. To attenuate noise in the image data, several frames of data may be retrieved and averaged for each pixel. This averaged pixel data may then be stored in buffer 32 for processing by processor 34.

Prior to initiation of thermal treatment, a treating physician preferably selects a region of interest within the image displayed on display 26, although the entire display may be identified as the region of interest. The region may be identified by using a mouse or trackball 52 to outline the region of interest. System 14 evaluates the image data within the region of interest during the monitoring period for temperature mapping. Preferably, the region of interest is defined by clicking on a first and second location on display 26 to define an upper left and lower right corner of a rectangle or square, although other predefined region shapes may be used. Once the region of interest is defined, processor 34 segregates the region of interest into predefined groups of pixels for temperature mapping. A group of pixels may be defined as a single pixel. However, such image segregation is sensitive to changes in position of the ultrasound probe. A small change in ultrasound probe position may substantially alter the pixel data being generated for the image and result in differential measurements that do not accurately reflect tissue changes. Preferably, the groups of pixels contain multiple pixels and are square in shape, although other shapes may be used. Multiple pixel groups are not as sensitive to ultrasound probe position changes. Preferably, the groups of pixels segregate the region of interest into an integral number of pixel groups. For example, a 160×160 pixel group may be segregated into 4×4, 10×10, or 16×16 groups of pixels.

Once the region of interest and groups of pixels are defined, processor 34 preferably generates a neural element for each group of pixels and builds a learning set of baseline values and transfer functions for each neural element. The baseline values are stored in learning set memory 36. Baseline values for a group of pixels are discussed in more detail below. The baseline values provide information to processor 34 about the homogeneity of a group of pixels and its surrounding neighborhood. This baseline information may be used to detect changes caused by thermal treatment which are correlated to temperature values and changes.

One set of baseline values for a group of pixels may include a differential measurement of the grayscale values within and outside a group of pixels. For example, an average grayscale value for a group of pixels may be computed and differential grayscale value for each pixel bordering the pixel group may be calculated and accumulated. Such a measurement provides an indication of the smoothness of the image in the area of the pixel groups. Likewise, gradients related to grayscale values at the boundaries of a pixel group may be used to define the change in an image area prior to initiation of thermal treatment. Other examples of baseline values include the detection, counting, and measurement of edges in the vicinity of a pixel group. Such edge detection and measurement may be performed using threshold, gradient, and Canny techniques, which are well known in the art.

Preferably, edge detection and measurement is performed using the radial techniques disclosed in U.S. Pat. No. 5,267,328. The techniques discussed in that patent which are used in a preferred embodiment of the invention include the radial shape extraction, radial spatial distribution extraction, radial contour extraction, and radial gradient extraction techniques. These techniques provide a baseline measurement for detecting and counting of edges in the vicinity of a pixel group, the smoothness of the image in the area of the pixel group, the homogeneity of the area around the pixel group, the similarity of the areas on opposing sides of the pixel group, a measure of the amount of grayscale change in the area of the pixel group, respectively. By using these techniques to establish baseline values and then compute changes in these values as thermal treatment occurs, differential values indicative of the amount of change caused by the treatment may be discerned.

After treatment begins, processor 34 uses the pixel values stored in buffer 32 for new frame data to generate new descriptors of the image currently being displayed. These descriptors are compared to the learning set data in learning set memory 36 to measure an image change for each group of pixels within the region of interest. The measured image change, typically expressed in grayscale units, is correlated to temperature change for the tissue area corresponding to the pixel group. This temperature change is compared to thresholds for the temperature ranges to ascertain the range in which the tissue resides. Identification of a temperature range for a pixel group is then used to generate overlay image data which is stored in overlay buffer 40. The overlay image data is converted to analog frame data and provided to display 24 by frame transmitter 42. The overlay image data colorizes portions of the image on display 24 to indicate temperature for tissue areas corresponding to the groups of pixels. Alternatively, the overlay image data may remain in pixel form and frame transmitter 32 may be an I/O controller for communicating the pixel data to system 12. The pixel data may be stored in the video RAM of system 12 and used to colorize a portion of display 24 to indicate temperature ranges for each group of pixels.

A sample neural element is shown in FIG. 3A. The neural element HI implements a transfer function which correlates the input data I to an output condition O. If an actual reading of the output condition is possible, the difference between the correlated output condition O and the actual condition is used to modify the transfer function so it better correlates the input data I to a corresponding output condition O. In this way, the element HI adjusts or learns during an ongoing process. In the present invention, this adjustment in the neural elements permits the system to compensate for changes in the tissue caused by blood perfusion or the like.

An exemplary neural element of the present invention is shown in FIG. 3B. Here the neural element HI receives four inputs, D1, D3, D5, and D7. These inputs are discussed in more detail below. These inputs define a set of descriptors for the neural element and the neural element corresponds to a pixel or group of pixels identified by the process discussed above. The descriptors D1, D3, D5, and D7 are derived from the pixel values in buffer 32. The transfer function in element HI of FIG. 3B correlates the difference between a weighted average of the current set of descriptors and a baseline condition for the descriptor set contained in the learning set to a temperature for the pixels corresponding to the element HI. This temperature results in activation of one of the four outputs. The outputs indicate whether the temperature is in the normal range (O1), the hyperthermic range (O2), the thermal therapeutic range (O3), and the ablative range (O4). Preferably, these ranges correspond to the ones expressed in degrees Celsius noted above. The use of four descriptors for a neural element is merely exemplary and more or fewer descriptors may be used for each element. Preferably, four descriptors are used for each neural element.

Preferably, at least one temperature probe 48 is implanted in the tissue which is being displayed. The signal from this probe 48 is converted by analog-to-digital converter 50 to a digital signal which is provided to the neural element in processor 34 which corresponds to the location in the displayed tissue where probe 48 is implanted. This signal provides an actual temperature reading which may be used to correct the transfer function for the neural element. This compensation factor may also be provided to the other neural elements to adapt the neural elements to ongoing conditions in the tissue being treated.

A preferred neural network for each group of pixels is shown in FIG. 3C. That network shows four inputs for a set of four descriptors, although fewer or more descriptors may be used for a group. The descriptors are measurements between a group of pixels and its neighbor groups. These inputs are each provided to four neural elements which weight them differently to compute a weighted average. These weighted averages are each applied to the output elements, one of each corresponds to a temperature range. The output elements weight the applied averages and one of the output elements is activated. Preferably, the output elements are also provided with a temperature correlation factor to verify whether the correct output element was activated. If there are any errors, an adjustment signal is generated and supplied to the neural elements providing the erroneous weighted average to adjust the weighting factors w at the neural element. The states of the output elements for each group of pixels are used to generate the overlay data.

The pixels which may be used to generate a set of descriptors for a pixel are shown in FIG. 4A. In that FIG., the center pixel P0 is the pixel for which a temperature is to be calculated. The immediately adjacent pixels P1–P8 are used to define descriptors D1–D8. These descriptors are defined by the difference between P0 and one of the adjacent pixels. For example, D1 is defined by the difference in the grayscale value of P0 and P1, D2 the difference between P0 and P2, and so on. The second nearest neighbors may also be utilized in the edge detection and measurements. In FIG. 4B, pixels P1–P8 are the nearest neighbors of center pixel P0 and pixels P9–P24 are the second nearest neighbors. Second nearest neighbors are preferably given less weight in the measurements than nearest neighbors. A weighted average of all or some of these descriptors may be used to define a set of descriptors for P0. In a similar manner, a set of descriptors may be defined for a group of pixels. As shown in FIG. 4B, the group of pixels denoted by G0 are surrounded by pixel groups G1–G8. In such a case, descriptor D1 may be defined by the average of the difference between each of the pixels in the top row of G0 and the vertically adjacent pixels in G1. Descriptors D3, D5, and D7 may be similarly defined. Descriptors for D2, D4, D6 and D8 may be defined by a difference between the corner pixel of G0 and the diagonally adjacent pixel in the G2, G4, G6 and G8 regions, respectively.

Preferably, the set of descriptors for a group of pixels are derived from eight radials about a pixel group. The radials, R1–R8 for a single pixel, are shown in FIG. 4A. In FIG. 4B, the radials may correspond to the eight surrounding groups about the center region G0 or they may be defined as the single row, column and diagonal radials extending from the center pixel of G0. The important aspect of selecting a set of descriptors is to define neighboring pixels in groups which provide information about the area about a pixel group so changes may be detected as they approach a pixel group or as they emanate from a pixel group.

The method of the present invention may be expressed in a flow chart as shown in FIG. 5. The treating physician preferably begins by adjusting the intensity of the displayed image on the display 22 (Step 100) so that the brightest element on the display can increase in intensity to a grayscale level that corresponds to the ablative temperature threshold of approximately 65° C. This may be done by adjusting the gain of the display so the intensity levels for the displayed image appear to be in the lower portion of the range of the grayscale. That is, the brightest points do not appear to be so "bright" or "white" that they cannot get much brighter without reaching the end of the upper range of the grayscale. Preferably, processor 34 generates a display which indicates the count of the pixels at various levels of grayscale intensities. The user adjusts the gain on the display until the number of pixels at the lower levels dominate the region of interest. In that way, the user shifts the displayed image to intensity levels which permit the pixels to change to the higher end of the grayscale which in turn makes higher temperature mapping possible.

After the grayscale intensity has been adjusted, the user may define a region of interest as discussed above (Step 102). The region of interest is then segregated into groups of pixels (Step 104). After groups of pixels are defined, a set of descriptors is selected for each pixel group and a transfer function which best maps the selected set of descriptors to the detected normal temperature is selected (Step 106). The descriptors may be differential measurements, gradients or the like which provide an indication of the homogeneity in the area of each pixel group. Baseline values for each descriptor in the set is determined and placed in the learning set memory associated with the neural element (Step 108). Mapping system 14 may then signal the treating physician that the system is ready and tissue treatment may begin. This indication may be generated by displaying a message on display 28, by energizing a light or light emitting diode ("LED") or other known visual or audible methods for indicating a computer system status.

As treatment begins, frame grabber 30 of system 14 periodically captures image data from system 12 and stores it in buffer 32 (Step 110). Upon receipt of this pixel data, the descriptors for the set of descriptors for each neural element are updated and input to the neural elements (Step 112). The neural elements compute a current element value using the descriptor inputs and measure the differential between the current element value and the baseline value (Step 114). The current value is also stored in working memory 38 to build a histogram for each neural element (Step 116). Preferably, the actual temperature for the tissue in which the temperature probe is implanted is read and the differential change in temperature from the starting temperature is measured. This change is correlated to the change in grayscale value between the baseline set of descriptors for the corresponding neural element and the current value (Step 118). If this grayscale unit to Celsius degree correlation factor is approximately the same as the one being used by the neural elements, the process continues (Step 120). Otherwise, the correlation or weighting factors for the transfer functions of the neural elements are modified (Step 122).

Using the grayscale/temperature correlation factor, each neural element computes a temperature change corresponding to the grayscale differential between the baseline value for the descriptor set and the current value (Step 124). The temperature differential is added to the measured starting temperature to determine the temperature for the tissue corresponding to the neural element (Step 126). If this temperature is greater than one of the threshold temperatures for the thermal treatment ranges (Step 128), overlay data corresponding to the detected temperature range is generated and stored in the overlay buffer 40 (Step 130). The overlay data is converted by frame transmitter 42 to a video signal which is transmitted to display 24 (Step 132) to produce a color change indicative of the temperature for a feature corresponding to a group of pixels.

The expert system described above uses one or more temperature probes to confirm the grayscale-to-temperature correlation factor. In an alternative embodiment, no temperature probes are used. Instead, the physician directs the treating probe at a tissue region being imaged and delivers a short burst of treating radiation. The power of this radiation and its duration is provided to the mapping system which uses this information with a tissue energy absorption factor to calculate a power deposition for the tissue. The power deposition corresponds to a known temperature change for the type of tissue identified for the feature. This temperature change is correlated to the grayscale differential measured for the same region during the test pulse. This is done two or three times to confirm or calculate an average correlation factor for the region. A corresponding correlation factor for other tissue types may be extrapolated from that data using known methods. Once the correlation factor is calibrated in this manner, use of the system proceeds as described above except the steps related to using the temperature measured by the probe to adjust the system are not performed.

Additionally, the expert system of the present invention may verify that the grayscale differential is thermally induced and not caused by signal noise. To verify the differential, the expert system may use edge detection techniques on the histogram data stored for a neural element to determine whether the gradient established by prior descriptor values confirms the shift in temperature range. Additionally, differences between a current descriptor set value for one neural element and the current descriptor set value for its neighboring neural elements may also be evaluated using edge detection or imaging enhancement techniques to confirm whether the area in the vicinity of the neural element is approaching or in another temperature range. Additionally, or alternatively, the histogram data may be processed using filtering or other noise alternating techniques to determine whether the current descriptor set accurately defines a tissue or image change. Thus, the histogram image data for each neural element and the descriptor set values for neighboring neural elements may be used to confirm the temperature shift for a region. This verification is used to reduce the likelihood of a temperature change indication being generated in response to noisy or aberrant data.

In use, the treating physician prepares a patient for thermal treatment of a targeted tissue area. Prior to initiating the treatment, the temperature monitoring system 10 is setup proximate to the patient and, if temperature probes are going to be used for temperature verification, they are inserted in the tissue which is to be displayed on the ultrasound image screen. After the temperature mapping system 14 has established baseline values for the descriptor sets for each neural element, the system signals the physician that treatment may begin. The treating physician then inserts the treating probe into a patient by a selected method and directs the emitted energy towards the target area. As heat is generated by the emitted energy in the target area, the mapping system 14 periodically captures pixel data being written to the video RAM 22. The captured data is used to update the descriptor values which are compared to the baseline values to generate a grayscale differential. The update rate depends upon the digital signal processor sued and the speed and amount of memory. In the preferred embodiment, the oculus F/64 card updates video data at a rate of 12 frames/second. The grayscale differential is correlated to a temperature change by using a grayscale-to-temperature correlation factor. The corresponding temperature determined for the tissue corresponding to the neural element is compared to the threshold temperatures for the treatment ranges. If the differential for a pixel value indicates that the temperature of the tissue has shifted to another zone, the mapping system may confirm the temperature zone shift by using edge detection techniques on the histogram data for the neural element or by using edge detection techniques on the descriptor set values for the neural elements adjacent to the neural element under investigation. Preferably, the mapping system reads one or more temperature probes implanted in the tissue to confirm the grayscale-to-temperature correlation factor used by the neural elements. When a temperature range shift is detected for the tissue corresponding to a neural element, the mapping system 14 stores color overlay data in the overlay buffer 40 which is transmitted to the video RAM 22 to modify display 24 of ultrasound unit 12. As the treating physician observes the addition of color to the displayed image, she may move the probe or adjust the energy being supplied to the target area. Once the treating physician is satisfied that the target area tissue has been necrosed or ablated, the treatment may cease and the treating probe removed. If the treating physician desires to continue temperature monitoring of the area, transmitter/transducer unit 18 is used to continue the generation of image data which is compared to the baseline by the expert system to indicate temperature change in the tissue.

Figure 6:
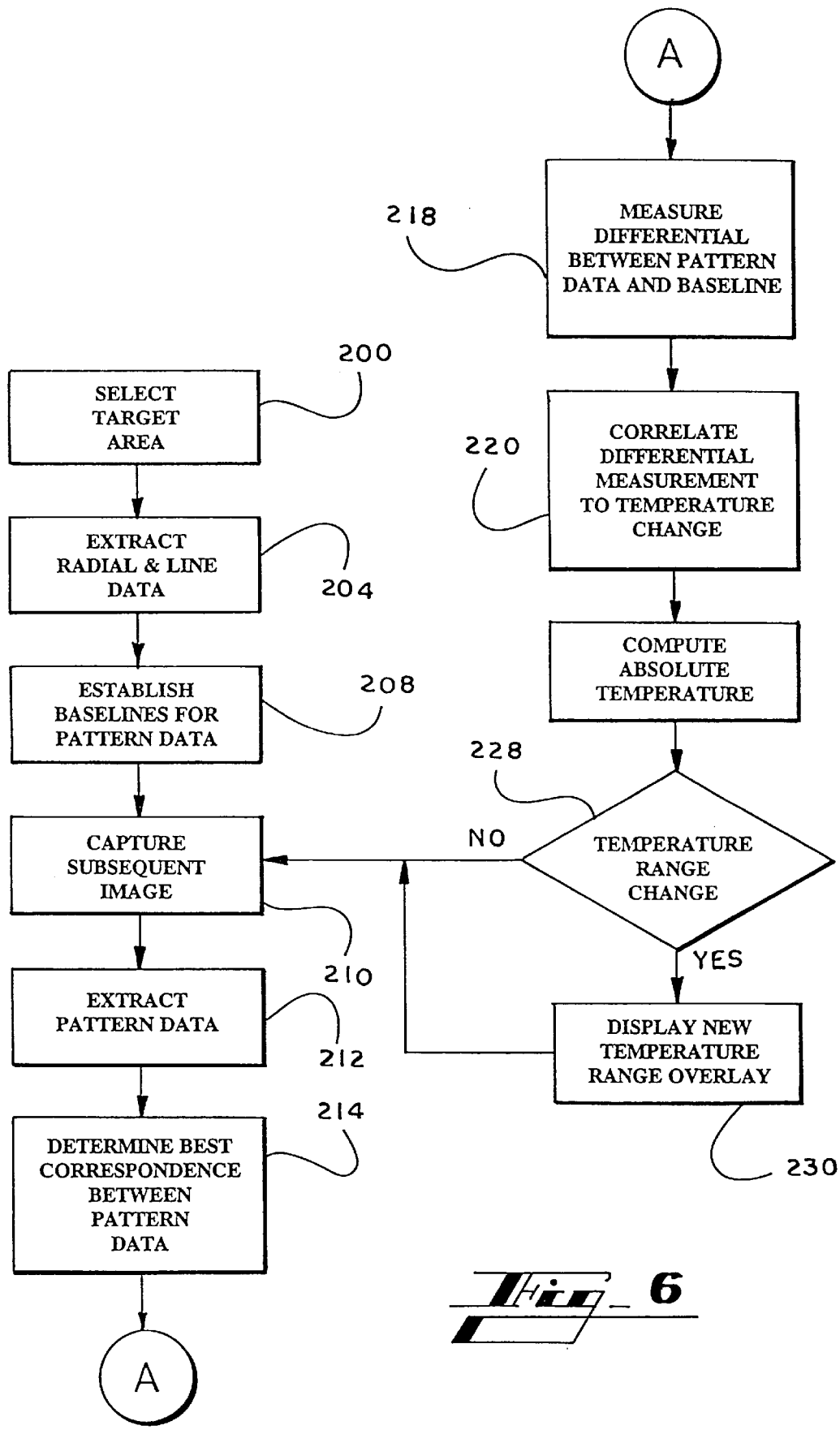
FIG. 6 is a flowchart of a method for monitoring temperature of tissue by extracting geometric shape data from the image.

A method for mapping temperature change which uses the Gouge pattern extraction and encoding method is shown in FIG. 6. Again, a group of pixels is selected as a target area in an image of tissue (Block 200). An initial image of this target area is then processed to extract pattern data such as radial and line data from the target pixels within the target area (Block 204). The extraction of the pattern data is performed in accordance with the Gouge method. The radial pattern data extracted from the target area includes radial shape data, radial spatial distribution data, radial contour data, radial asymmetry data, and radial gradient data. Likewise, line pattern data may be extracted from the target pixels of the target area in accordance with the Gouge method and the pattern data such as the radial and line data are used to extract geometric shape data from the target area. The pattern data extracted from the target area are used to establish baselines for the target area (Block 208). Once treatment begins, subsequent images of the target area are obtained and processed using the Gouge method to determine changes in pattern data for the target area (Blocks 210, 212). A best correspondence between pattern data in the subsequent image and pattern data in the initial image is determined by comparing the pattern data extracted from the subsequent image to the knowledge trees for the pattern data of the initial image (Block 214). Differential measurements between the pattern data for the subsequent image and the baseline for the best corresponding pattern data in the initial image are computed (Block 218). These differential measurements are then correlated to temperature changes by correlation factors derived from previously obtained empirical temperature measurements (Block 220). The process then adds the temperature change to the last absolute temperature for the extracted pattern data (Block 224). The resulting absolute temperature is then compared to the temperature ranges to determine whether the temperature indication for the overlay corresponding to the extracted pattern data should be changed for the display (Block 228).

If the new absolute temperature crosses the threshold, the overlay indication on the display is changed to correspond to the new temperature range (Block 230).

While the present invention has been illustrated by a description of preferred and alternative embodiments and processes, and while the preferred and alternative embodiments and processes have been described in considerable detail, it is not the intention of the applicant to restrict or in any way limit the scope of the appended claims to such detail. Additional advantages and modifications will readily appear to those skilled in the art. For example, the change in the backscattered data may be detected in the signals received by the transmitter/transducer unit 18. As a result, the signals generated by the transducers in unit 18 may be processed by a system built in accordance with the principles of the present invention to determine temperature changes. Such a system is within the scope of the present invention. Likewise while the invention has been described with reference to images generated by ultrasound energy, the system and method of the present invention may also be used with image data generated from radar or other imaging energy sources.

What is claimed:

1. A method for mapping temperature changes in tissue comprising:
    receiving an image of tissue comprised of multiple pixels;
    segregating said image into groups of pixels, each said group of pixels having a corresponding set of descriptors derived from said pixels in said corresponding group of pixels;
    establishing a baseline for at least one of each group of pixels and said corresponding set of descriptors, said baseline corresponding to initial conditions of the tissue as a learning set;
    measuring a differential between said set of descriptors for a group of pixels which correspond to new pixels within a group of pixels and said baseline for said set of descriptors for said group of pixels;
    correlating said measured differential to a temperature change for the tissue corresponding to said group of pixels; and
    overlaying an indication of temperature over the tissue image in response to said correlated temperature change indicating a change in temperature range for the tissue.

2. The method of claim 1, said segregating step further comprising the step of:
    defining a region of interest in said image of tissue; and
    segregating said region of interest into groups of pixels.

3. The method of claim 1, said segregating step further comprising the step of:
    selecting said set of descriptors for each group of pixels from a set of descriptors formed by a differential measurement between pixels within said group and pixels outside said group.

4. The method of claim 1, said correlating step further comprising:
    reading an actual temperature measurement corresponding to one of said groups of pixels;
    measuring a grayscale differential between said baseline for said one group of pixels; and
    correlating said grayscale differential to a difference between said actual temperature measurement and a baseline temperature measurement.

5. The method of claim 4 further comprising the step of:
    adjusting a grayscale-to-temperature correlation factor for said other groups of pixels in correspondence with said correlated grayscale to temperature measurement.

6. The method of claim 1, said establishing baseline step further comprising:
    calibrating a grayscale-to-temperature correlation factor from a plurality of power deposition measurements.

7. The method of claim 1, said modifying step further comprising the steps of:
    generating overlay data corresponding to said predetermined temperature ranges, said overlay data comprising a color for each of said predetermined temperature ranges.

8. A system for mapping temperature changes in tissue comprising:
    a buffer for receiving video data corresponding to an image generated for an ultrasound system;
    a processor for establishing baseline values from video data corresponding to at least one region of said image and generating descriptors for said region derived from video data corresponding to said region, said video data for generating said descriptors being received subsequent to said video data used to establish said baselines;
    a comparator for comparing said generated descriptors to said established baselines to measure image change;
    a correlator to correlate said measured image change to a temperature range; and
    an overlay generator for generating overlay image data for modifying said image to indicate said region being in said correlated temperature range.

9. The system of claim 8, said comparator and said correlator being implemented in a neural network of neural elements, each of said neural elements implementing a transfer function for correlating measured image change to a temperature range.

10. The system of claim 9, said neural elements further including:
    input for temperature data about tissue corresponding to said image; and
    said neural element modifying said transfer function in correspondence to said temperature data so that said transfer function more accurately correlates said measured image changes to said temperature range.

11. A method for mapping temperature changes in tissue comprising the steps of:
    segregating an image of tissue comprised of multiple pixels into a target area of target pixels;
    extracting pattern data from said target area in an initial image of the tissue to establish a baseline for each pattern in said pattern data extracted from said initial image;
    extracting pattern data from said target area in a subsequent image of said tissue;
    determining a best correspondence between said extracted pattern data in said subsequent image and said extracted pattern data in said initial image by comparing said extracted pattern data in said subsequent image with said pattern data in said initial image;
    measuring a differential between said extracted pattern data from said subsequent image and said established baseline for said extracted pattern best corresponding to said pattern data in said initial image;
    correlating a temperature change to said measured differential for said extracted pattern data in said subsequent image; and overlaying an indication of temperature range over a portion of said target area corresponding to said correlated temperature change to indicate a change in temperature range.

12. The method of claim 11, said extracting pattern data steps further comprising the steps of:

extracting radial data about said target pixels within one of said initial image and said subsequent image; and extracting line data for said target pixels within one of said initial image and said subsequent image.

13. The method of claim 12, said extracting radial data step further comprising the step of:

extracting for each target pixel radial shape data, radial spatial data, radial contour data, radial asymmetry data, and radial gradient data.

14. The method of claim 12 further comprising the step of extracting geometric shape data from said extracted radial and said extracted line data.

* * * * *